(12) United States Patent
Reydel

(10) Patent No.: US 9,775,496 B2
(45) Date of Patent: Oct. 3, 2017

(54) DISPOSABLE AND REUSABLE COMPLEX SHAPED SEE-THROUGH ENDOSCOPE

(71) Applicant: Visualization Balloons, LLC, West Caldwell, NJ (US)

(72) Inventor: Boris Reydel, West Caldwell, NJ (US)

(73) Assignee: Visualization Balloons, LLC, West Caldwell, NJ (US)

( * ) Notice: Subject to any disclaimer, the term of this patent is extended or adjusted under 35 U.S.C. 154(b) by 576 days.

(21) Appl. No.: 14/538,283

(22) Filed: Nov. 11, 2014

(65) Prior Publication Data

US 2015/0133729 A1 May 14, 2015

Related U.S. Application Data

(62) Division of application No. 13/501,803, filed as application No. PCT/US2010/052947 on Oct. 15, 2010, now abandoned.

(60) Provisional application No. 61/278,970, filed on Oct. 15, 2009.

(51) Int. Cl.
| | |
|---|---|
| *A61B 1/04* | (2006.01) |
| *A61B 1/00* | (2006.01) |
| *A61B 1/31* | (2006.01) |
| *A61B 1/12* | (2006.01) |

(52) U.S. Cl.
CPC ............ *A61B 1/04* (2013.01); *A61B 1/00082* (2013.01); *A61B 1/00101* (2013.01); *A61B 1/00137* (2013.01); *A61B 1/00142* (2013.01); *A61B 1/12* (2013.01); *A61B 1/31* (2013.01)

(58) Field of Classification Search
USPC ................ 600/115–116; 606/96.01–103; 604/101.01, 101.02, 101.04, 103.05
See application file for complete search history.

(56) References Cited

U.S. PATENT DOCUMENTS

| | | |
|---|---|---|
| 3,417,745 A | 12/1968 | Emanuel |
| 3,690,769 A | 9/1972 | Mori |
| 3,866,599 A | 2/1975 | Johnson |
| 4,619,247 A | 10/1986 | Inoue et al. |
| (Continued) | | |

FOREIGN PATENT DOCUMENTS

| | | |
|---|---|---|
| EP | 0112148 | 6/1984 |
| JP | 63/201504 | 8/1988 |
| (Continued) | | |

OTHER PUBLICATIONS

Office Action from European Application No. 10824218.1 dated Mar. 1, 2013.
(Continued)

*Primary Examiner* — Matthew J Kasztejna
(74) *Attorney, Agent, or Firm* — Meunier Carlin & Curfman LLC

(57) ABSTRACT

Transparent domes useful for covering at least a lens located on a scope's distal face, taking the form of a single layer membrane affixed to the distal end of the scope, a solid cap attachable to and detachable from the distal end of the scope, or an inflatable and deflatable balloon having an exterior wall for contacting at least the lens at the scope's distal face. Methods for performing diagnostic or diagnostic and therapeutic procedures within bodily cavities including collapsed intestines using transparent domes and scopes.

15 Claims, 14 Drawing Sheets

(56) References Cited

U.S. PATENT DOCUMENTS

| | | |
|---|---|---|
| 4,681,093 A | 7/1987 | Ono et al. |
| 4,841,952 A | 6/1989 | Sato et al. |
| 4,961,738 A | 10/1990 | Mackin |
| 5,002,556 A | 3/1991 | Ishida et al. |
| 5,029,574 A | 7/1991 | Shimamura et al. |
| 5,103,804 A | 4/1992 | Abele et al. |
| 5,257,617 A | 11/1993 | Takahashi |
| 5,271,383 A | 12/1993 | Wilk |
| 5,304,173 A | 4/1994 | Kittrel et al. |
| 5,337,730 A | 8/1994 | Maguire |
| 5,364,353 A | 11/1994 | Corfitsen et al. |
| 5,620,408 A * | 4/1997 | Vennes et al. ............... 600/114 |
| 5,681,344 A | 10/1997 | Kelly |
| 5,897,487 A | 4/1999 | Ouchi |
| 6,059,719 A | 5/2000 | Yamamoto et al. |
| 6,306,081 B1 | 10/2001 | Ishikawa et al. |
| 6,423,055 B1 | 7/2002 | Farr et al. |
| 6,953,431 B2 | 10/2005 | Barthel |
| 2002/0068853 A1 | 6/2002 | Adler |
| 2003/0233142 A1 | 12/2003 | Morales et al. |
| 2005/0049461 A1 | 3/2005 | Honda et al. |
| 2005/0288522 A1 | 12/2005 | Vogel et al. |
| 2006/0025654 A1 | 2/2006 | Suzuki et al. |
| 2006/0106414 A1 | 5/2006 | Fogarty et al. |
| 2007/0015966 A1 | 1/2007 | Niwa et al. |
| 2007/0249907 A1 | 10/2007 | Boulais et al. |
| 2007/0276180 A1 | 11/2007 | Greenburg et al. |
| 2007/0287885 A1 | 12/2007 | Brown |
| 2009/0082626 A1 | 3/2009 | Ichimura et al. |
| 2009/0287050 A1 | 11/2009 | Barthel |
| 2010/0274084 A1 | 10/2010 | Barthel |
| 2012/0232342 A1 | 9/2012 | Reydel |
| 2012/0259175 A1 | 10/2012 | Reydel et al. |

FOREIGN PATENT DOCUMENTS

| | | |
|---|---|---|
| JP | 01/221133 | 9/1989 |
| JP | 2005/503203 | 2/2005 |
| JP | 2007/175502 | 7/2007 |
| JP | 2008/212506 | 9/2008 |
| JP | 2009/534113 | 9/2009 |
| WO | 2011/047339 | 4/2011 |

OTHER PUBLICATIONS

Office Action for Japanese Application No. 2012-534419 dated Feb. 18, 2014.
International Search Report and Written Opinion in corresponding Application No. PCT/US2010/052947, dated May 27, 2011.
Preliminary Report on Patentability from corresponding International Application No. PCT/US2010/052947, dated Apr. 17, 2012, 6 pages.
International Search Report and Written Opinion for corresponding International Application No. PCT/US2012/032248, dated Jul. 2, 2012, 14 pages.

* cited by examiner

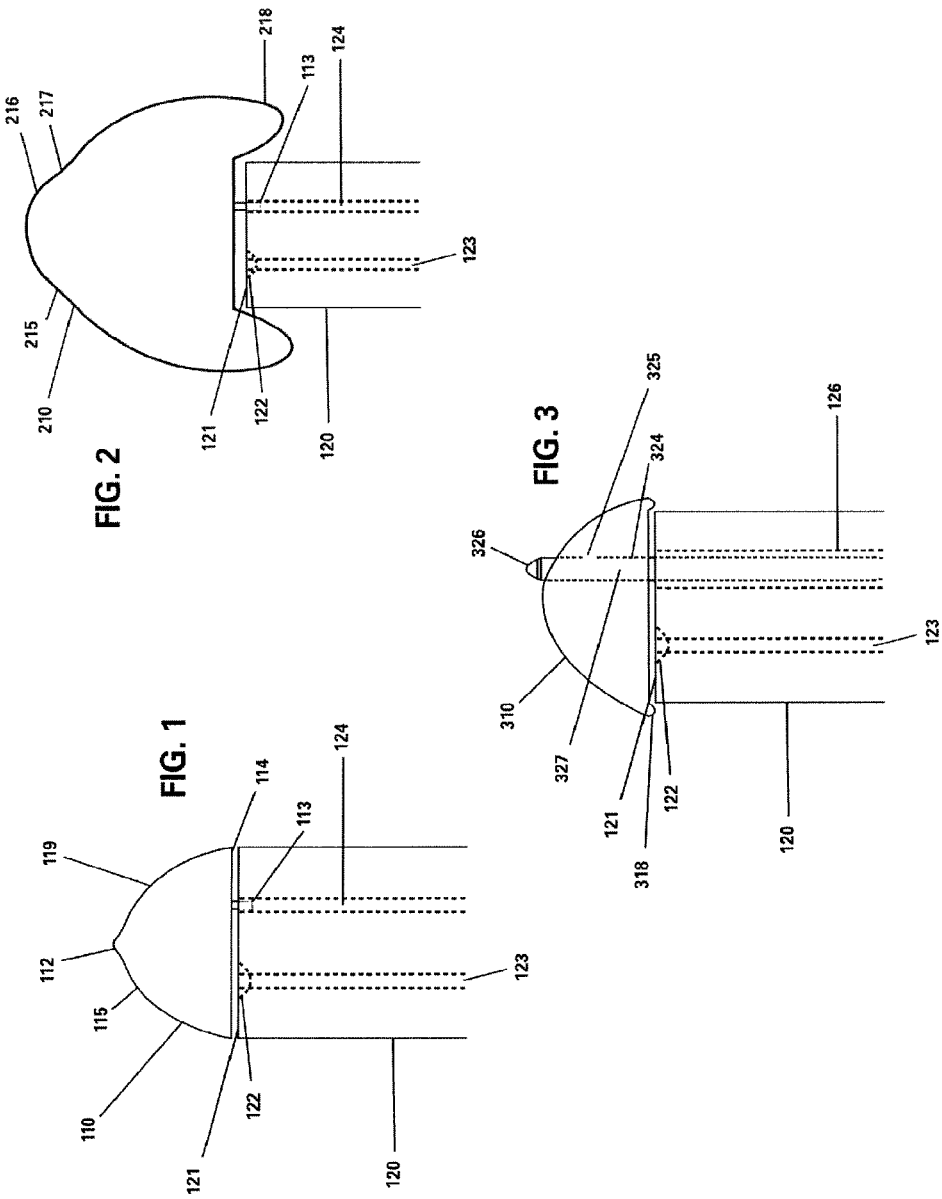

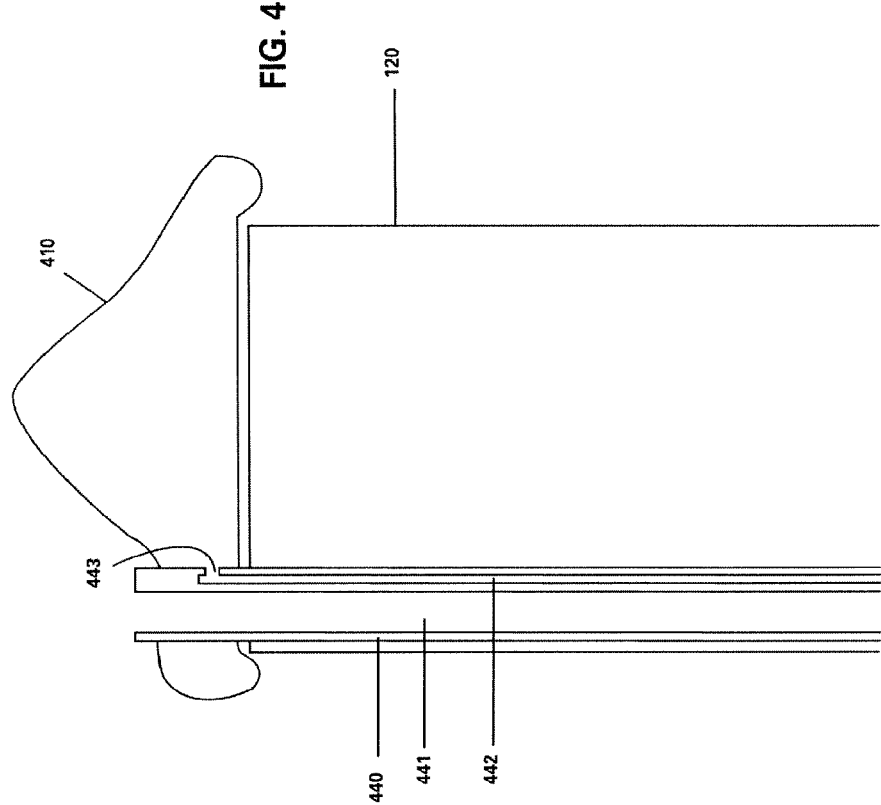

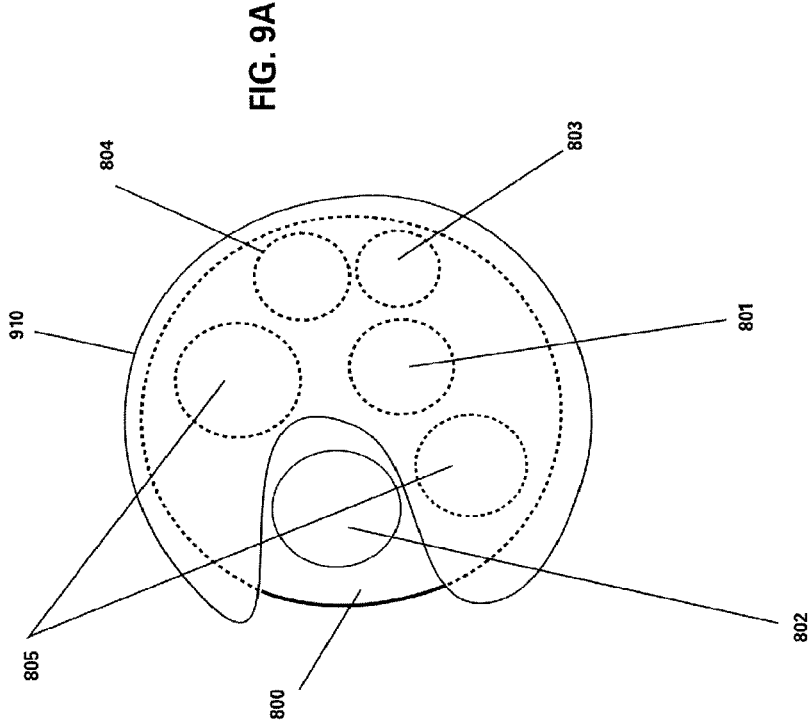

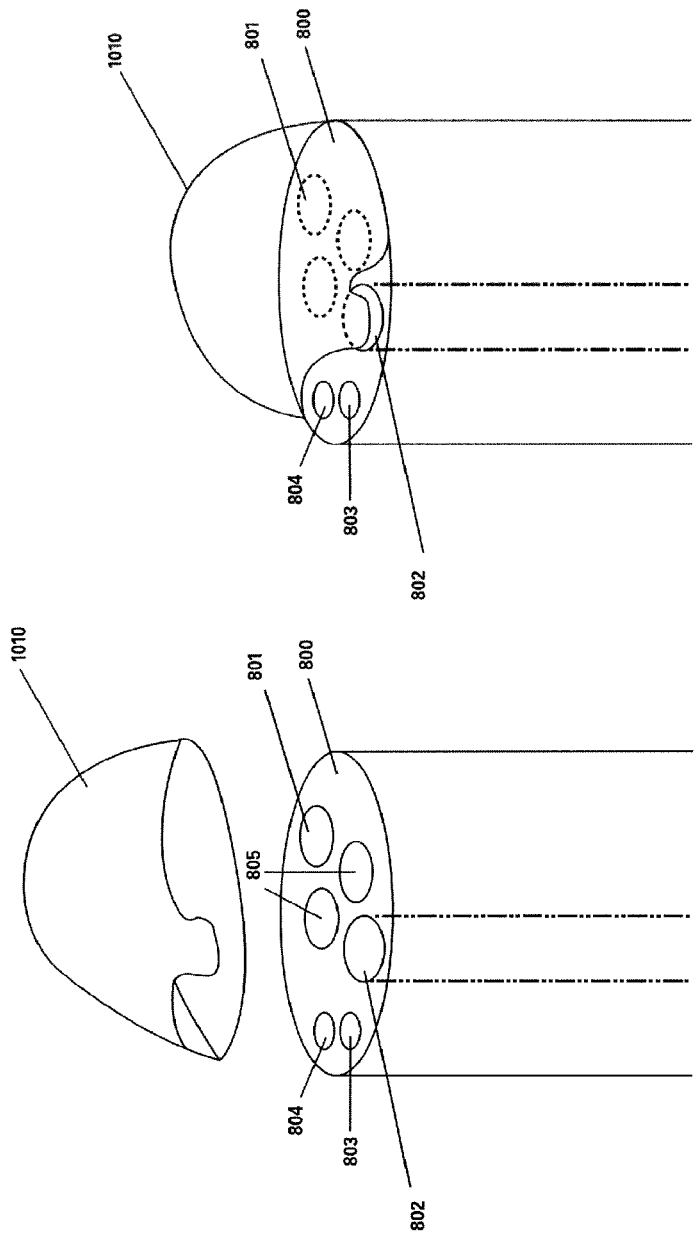

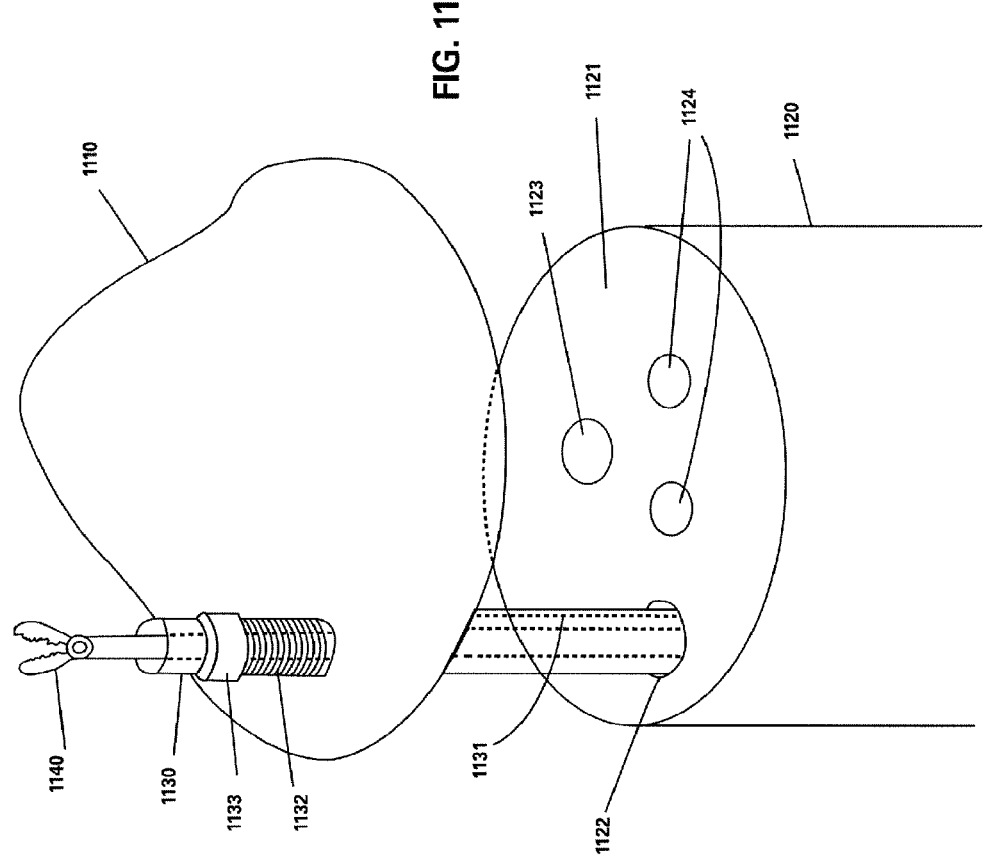

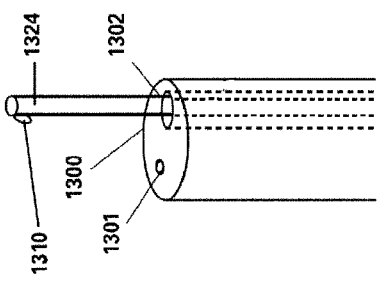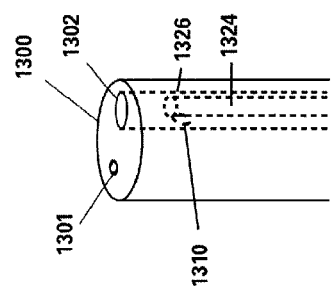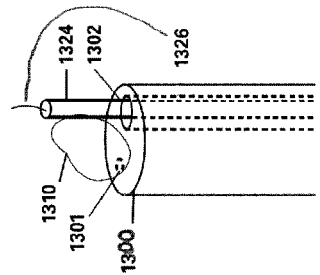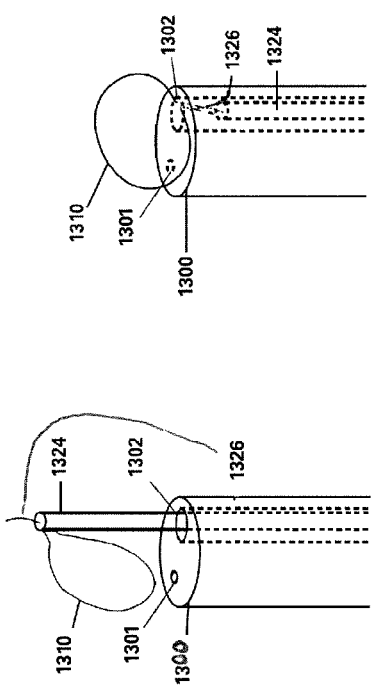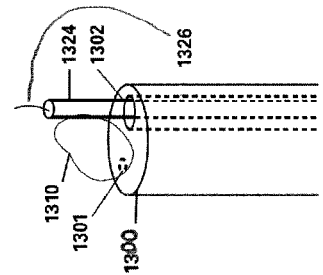
FIG. 13A
FIG. 13B
FIG. 13C
FIG. 13D
FIG. 13E

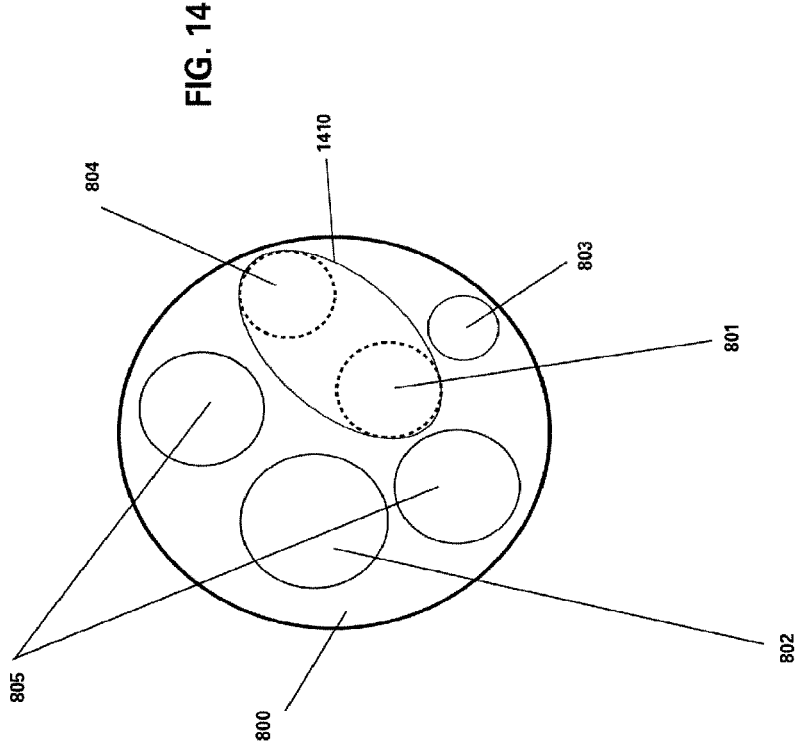

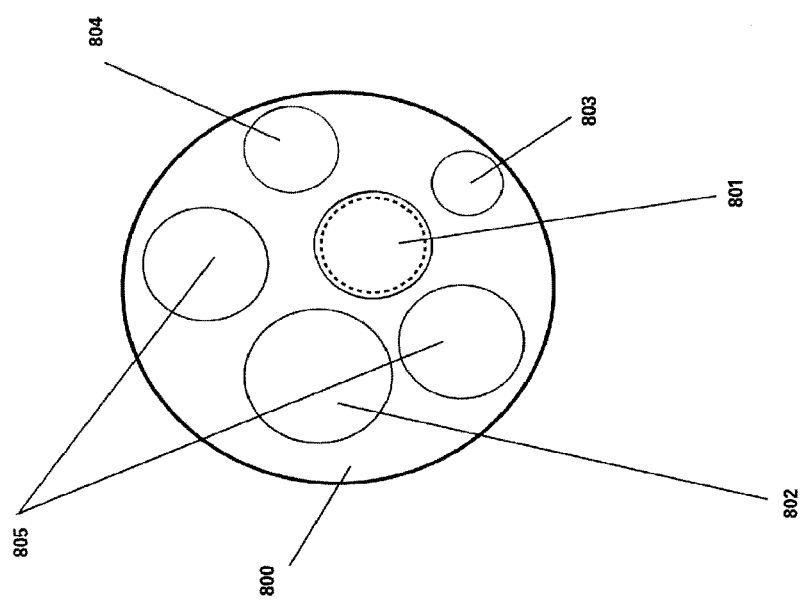

DISPOSABLE AND REUSABLE COMPLEX SHAPED SEE-THROUGH ENDOSCOPE

CROSS REFERENCE TO OTHER APPLICATIONS

This application is a Divisional of U.S. application Ser. No. 13/501,803 filed May 24, 2012, which claims priority to U.S. Provisional Application No. 61/278,970, filed Oct. 15, 2009, the contents of both of which are hereby incorporated by reference in their entirety.

FIELD OF THE INVENTION

The present invention relates generally to medical imaging systems and, more particularly, to imaging systems for insertion into a lumen of a patient for viewing the lumen through a transparent dome at the tip of the system, and to methods of use of such systems that take advantage of the transparent dome structure, which systems and methods are particularly useful in performing colonoscopies.

BACKGROUND OF THE INVENTION

Colonoscopy is a very common procedure. In the United States snore than 20 million such procedures are done every year. Colonoscopy is a relatively expansive procedure necessitating intravenous sedation to alleviate pain. The cause of pain may be due to several factors, including dilation and stretching of the colon during air insufflations from the colon's normal collapsed state resembling a collapsed tortuous hose, and including looping out and stretching fire nerve-laden colonic mesentery when a flexible colonoscope is pushed through multiple S-shaped curves in the colon. Some of these curves resemble, from the interior of the colon, a buckled-down hose. Recent studies show that if instead of air insufflations, water is used to open up the lumen, the colon gets stretched out but not as much as when the colon is opened with air, and the patient has mach less pain. Nonetheless, such use of water results in stretching of the colon and pain to the patient.

Additionally, traditional scopes used in colonoscopies have blunt edges which can damage or perforate the colon. These scopes also lend to cease transmitting a usable image when their distal ends come too close to the wall of the lumen.

Accordingly, there is a need for devices and methods useful for performing a colonoscopy that require minimal insufflation of the colon, so as to minimize stretching out of the colon and pain to the patient, while at the same time minimizing the chance of damaging or perforating the colon and maintaining a usable image transmission.

SUMMARY OF THE INVENTION

The present invention provides for the needs identified in the foregoing discussion by providing for a transparent dome useful for covering at least a lens located on a scope's distal face. In different embodiments of the present invention, the dome may comprise a single-layer membrane affixed to the distal end of the scope such that it also covers an air channel for inflating the transparent dome, or it may comprise a solid cap which is attachable to and detachable from the distal end of the scope, or it may comprise a balloon having an exterior wall for contacting at least the lens at the scope's distal face.

The present invention also provides for a transparent dome and a scope having a leas located at its distal face to be used by inserting the scope and the transparent dome into a bodily cavity and viewing, through the lens and the transparent dome, at least a portion of the bodily cavity. The present invention also provides for such a transparent dome and scope to be used by inserting the scope into a bodily cavity; using the lens of the scope, identifying a particular lesion of the bodily cavity; based on the identification of the particular lesion, advancing a catheter comprising a deflated transparent dome and a particular therapeutic tip chosen for its ability to treat the particular lesion, through an operative channel of the scope; inflating the transparent dome; and, under vision through the lens and the transparent dome, treating the particular lesion with the particular therapeutic tip of the catheter.

BRIEF DESCRIPTION OF THE DRAWINGS

FIG. 1 shows a first embodiment of a transparent dome according to the present invention in the form of a balloon at the distal end of a scope, the balloon having a flat bottom.

FIG. 2 shows an additional embodiment of a transparent dome according to the present invention in the form of a balloon at the distal end of a scope, the balloon having an overhanging portion.

FIG. 3 shows yet another embodiment of a transparent dome according to the present invention in the form of a balloon at the distal end of a scope, the balloon having a therapeutic tip.

FIG. 4 shows an additional embodiment of a transparent dome according to the present invention, the balloon being held by a catheter having an operative channel and a separate additional channel for inflating the balloon.

FIG. 9a shows a distal face of a scope partially covered by a plastic membrane having a crescent shape.

FIG. 9b shows a different view of the scope and inflated plastic membrane of FIG. 9a.

FIG. 10a shows a transparent dome according to the present invention in the form of a solid cap, and a scope to which the transparent dome may be attached.

FIG. 10b shows the transparent dome of FIG. 10a attached to the scope of FIG. 10a.

FIG. 11 shows an additional embodiment of a transparent dome in the form of a balloon along with a catheter, therapeutic device, and scope.

FIGS. 13a-e show a method for using a transparent dome in the form of a balloon, scope and catheter holding the balloon at the catheter's side.

FIG. 14 shows another embodiment of an inflated plastic membrane.

FIG. 15 shows an embodiment of an uninflated single-layer membrane.

DETAILED DESCRIPTION OF THE INVENTION

Figure 5B:
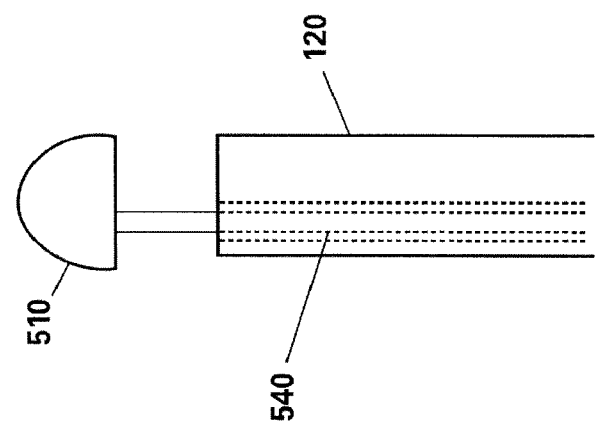
FIG. 5b shows the transparent dome of FIG. 5a positioned as a distance from the distal face of a scope.

FIG. 1 shows a transparent dome 110, in the form of art inflated balloon, covering the distal face 121 of a scope 120. The distal face 121 of the scope 120 has a lens 122 for transmitting image or video information so the scope's operator through the visual transmission channel 123. The transparent dome 110 has an exterior wall ill which contacts the distal face 121 of the scope 120, at least at the lens 122 of the distal face 121. In particular, the exterior wall 111 contacts the distal face at a flat region 114 at the proximal end of the transparent dome 110. The flat region 114 may be a result of the shape of the transparent dome 110, as opposed to a result of the application of pressure to the proximal end of the transparent dome 110. Although a slight space appears, for ease of labeling, in FIG. 1 between the flat region 114 of the exterior wall 111 and distal face 121, it will be understood that a contacting relationship is shown. The transparent dome 110 has a distal portion 115 which has a rounded shape and is generally convex. The transparent dome 110 also has a distal tip 112, which may be slightly pointed as shown. The structure of the transparent dome 110 is useful for pushing away a wall of the bodily cavity such as an interior of an organ, and this pushing away may substitute for air or water insufflations of the bodily cavity.

Because the wall of the bodily cavity is kept away from the lens 122, the operator avoids seeing only a red blot or similar obstruction, much like the effect when a camera operator touches his or her finger to the camera lens. Blood, clots, fecal material, and mucosa are all kept away from the lens 122 and prevented from obscuring it. The transparent dome 110 also transforms the blunt edge of the scope 120 into a smooth aerodynamic shape, thus decreasing the rate of perforation of the walls of the bodily cavity. As a result of these features, the distal end of the device may be inserted into a pool of blood in such locations as the fundus of the stomach and slid along the wall of the stomach until the point of bleeding is found. The transparent dome 110 may be made of any suitable material, such as a plastic. Preferably, it should be made from a material that is very transparent and which has a thin wall, so as not to distort the image or video received by the lens.

An air intake portion 113 of the transparent dome 110 connects the dome 110 with an air channel 124 and allows for air to be sent through the air channel 124, through the air intake portion 113 and into the transparent dome 110, thereby inflating it. The air channel 113 may be a channel of the scope 120, or it may be a catheter adapted for insertion into, and proximal and distal movement relative to, the scope 120.

The transparent dome 110 may have a color, such that it acts as a color filter for the lens 122. In particular, the color may be green, the transparent dome 110 acting as a green color filter for the lens 122. Such a green color filter is particularly helpful in allowing for easier recognition of flat lesions, such as those which may appear in a colon.

FIG. 2 shows another embodiment of a transparent dome 210, covering the distal face 121 of a scope 120. The distal portion of the transparent dome 210 has a convex region 216 at a maximally distal center, and a concave region 217 which is positioned radially outwards from the convex region 216. This creates an overall aerodynamic shape helpful in safely and easily inserting the device through the bodily cavity.

The transparent dome 210 also has an overhanging portion 218. The overhanging portion 218 may comprise a radially-outermost portion of the transparent dome 210 which extends, at a region of fire transparent dome 210 approximately as distal as the distal face 121 of the scope 120, radially outwards beyond the edge of the distal face of the scope. The overhanging portion 218 also comprises a portion that extends more proximally than the distal face 121 of the scope 120. Advantageously, when the scope 120 and transparent dome 210 are pulled proximally within a bodily lumen, frictional resistance between the overhanging portion 218 and the inner wall of the bodily lumen consistently slows the speed of the pulling, thereby preventing "slip-off," inconsistent rates of movement of the transparent dome 210 and scope 120 relative to the bodily cavity, and failing to see lesions through the lens 122 as a result.

Accordingly, a user may, after inserting the scope 120 and the transparent dome 210 into a bodily cavity, and while viewing, through the lens 122 and the transparent dome 210, at least a portion of the bodily cavity, pull the scope 120 and transparent dome 210 in a proximal direction through the bodily cavity under frictional resistance between the portion of the transparent dome 210 extending radially outwards beyond the edge of the distal face 121 of the scope 120 and the bodily cavity. Contacting the bodily cavity with the transparent dome 210 may also be used to flatten folds in the bodily cavity. Advantageously, this enlarges the potential field of view of the lens 122 when a fold is present, because in the absence of such a transparent dome 210 it would be necessary to deflect the fold with the distal face 121 of the scope 120 in order to see on the other side of the fold, and in the process there would be obstruction of the lens 122. The device could also help to visualize polyps on the distal sides of the folds where traditional scopes could not. Additionally, the transparent dome 210 may be pushed against an intestinal wall so as to open up the lumen of the bodily cavity and ease further distal advancement of the scope 120 and transparent dome 210 into the bodily cavity.

Moreover, a lesion in the bodily cavity may be palpated with the transparent dome 210, and the result of this palpation may be viewed through the lens 122 and the transparent dome 210. On the basis of this viewing, the hardness of the lesion may be determined. Alternately, a mucosal defect of the bodily cavity may be contacted with the transparent dome 210, and the result of this contacting may be viewed through the lens 122 and the transparent dome 210. On the basis of this viewing, such as by seeing whether the defect blenches, a user may differentiate between the mucosal defect being an abnormal sub-mucosal blood vessel and it being an intra-mucosal inflammation. The transparent dome 210 may also be used to apply direct pressure to a bleeding vessel of the bodily cavity to reduce bleeding. The various viewings may occur while at least the distal tip of the transparent dome 210 is in a pool of blood or is contacting a blood clot, as vision is maintained, unlike a situation where tire lens is directly exposed to the pool of blood or blood clot.

The bodily cavity may be a generally collapsed small bowel and the insertion and viewing may be accomplished without releasing air or water into the small bowel. This generally collapsed small bowel may belong to an unsedated or comparatively unsedated patient, as pain is greatly reduced by not insufflating (and thereby stretching) the bowel. Accordingly, the present invention is very useful in small bowel enteroscopy, the procedure being performed in a much shorter time and with less technical complexity than with conventional methods involving insufflations of the bowel.

FIG. 3 shows another embodiment of a transparent dome 310, covering the distal face 121 of a scope 120. A catheter 324 has art air channel 327 and an air hole 325 through which air may be sent to inflate the transparent dome 310. The scope 120 comprises an operative channel 126, the balloon being held by the catheter 324 which is inserted through the operative channel 126, the transparent dome 310 being held by the catheter 324 at a side region of the catheter 324. The transparent dome 310 may connect to the catheter only in the region of the air hole 325, or it may connect at its distal end to a region of the catheter 324 more distal than the air hole 325, and at its proximal end to a region of the catheter 324 more proximal than the air hole 325.

The catheter 324 further comprises a therapeutic device 326 attached to its distal tip and at least partially located more distal than the transparent dome 310. The therapeutic device 326 may be, but is not limited to, a sclerotherapy needle, bicap, laser probe, polypectomy device, small biopsy forceps, or the like.

FIG. 4 shows a cutaway view of another embodiment of a transparent dome 410 covering the distal face 121 of a scope 120. A catheter 440 comprises an air channel 442 for inflating the transparent dome 410, and an additional channel 444, separate from the air channel 442, opening distally to the distal side of the transparent dome 410. Advantageously, therapeutic medical devices may be inserted through the additional channel 444 to the distal side of the transparent dome 410, where they may be used in performing a procedure under direct vision through the lens and the transparent dome 410. The flat bottom region may completely cover the entire distal face 121 of the scope 120, thus lowering the chances of blood getting to the lens.

Figure 5A:
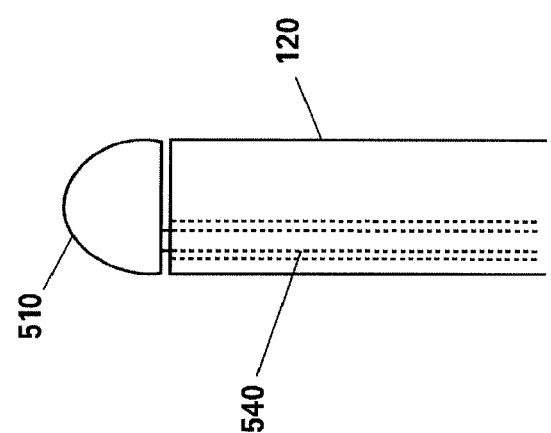
FIG. 5a shows another embodiment of a transparent dome according to the present invention positioned so that it is adjacent or nearly adjacent to the distal face of a scope.

FIGS. 5a and 5b show how a transparent dome 510 may be positioned at different distances from the distal face 121 of the scope 120. FIG. 5a shows the transparent dome adjacent or nearly adjacent to the distal face 121 of the scope 120, while FIG. 5b shows the transparent dome at an exemplary distance of 0.5 inches from the distal face 121 of the scope 120. Movement between these two positions between other relative distal positions can be accomplished through distal or proximal movement of the catheter relative 540 relative to the scope 120.

Figures 6A, 6B, 6C:
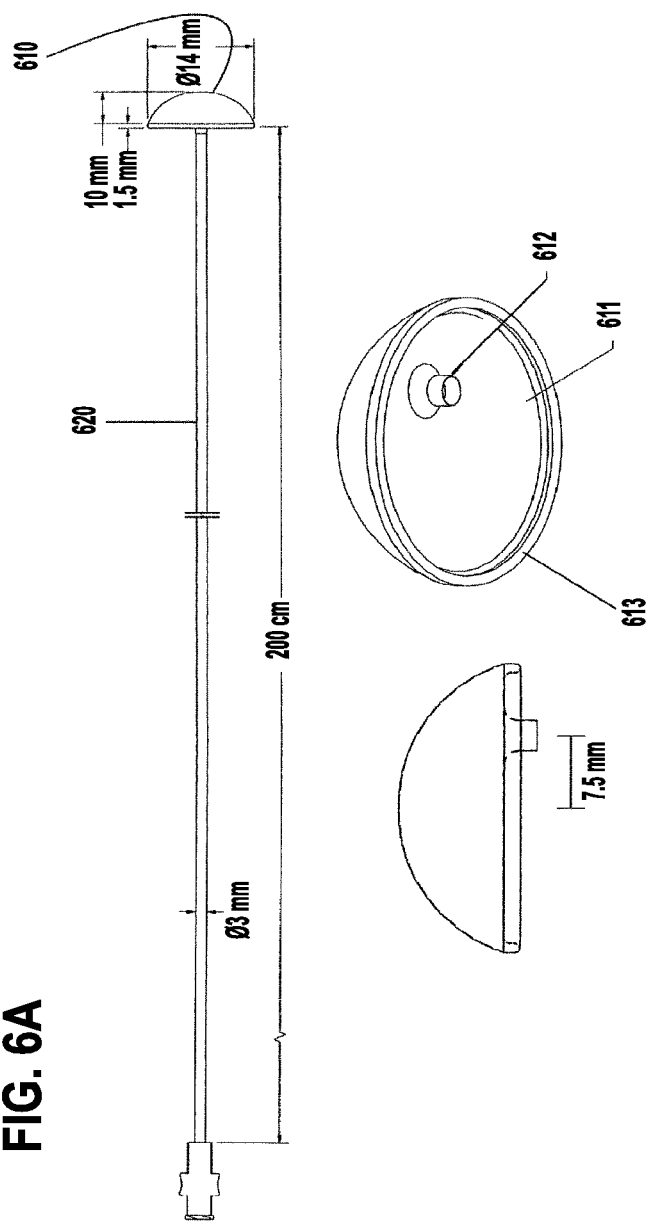
FIGS. 6a-c various views of an additional embodiment of a transparent dome with suggested dimensions, with FIG. 6a further showing a catheter.

FIG. 6a shows an additional embodiment of a transparent dome 610 and a catheter 620, with particular suggested dimensions. The catheter 620 should be long enough to extend through a scope, and accordingly is shown as 200 cm in length. The length may vary with tire length of the scope. The overhanging portion 613 may extend 1.5 mm proximally beyond the flat region 611. The transparent dome 610, from its flat region 611 to its distal tip may be 10 mm. The air intake portion 612 may be positioned 7.5 mm from the center of the transparent dome 610, as shown in FIG. 6c, or as necessary to fit a particular catheter or scope opening. FIG. 6b shows a side view of the transparent dome 616. FIG. 6c shows an angled view of the transparent dome 610 from below.

Figures 7A, 7B, 7C:
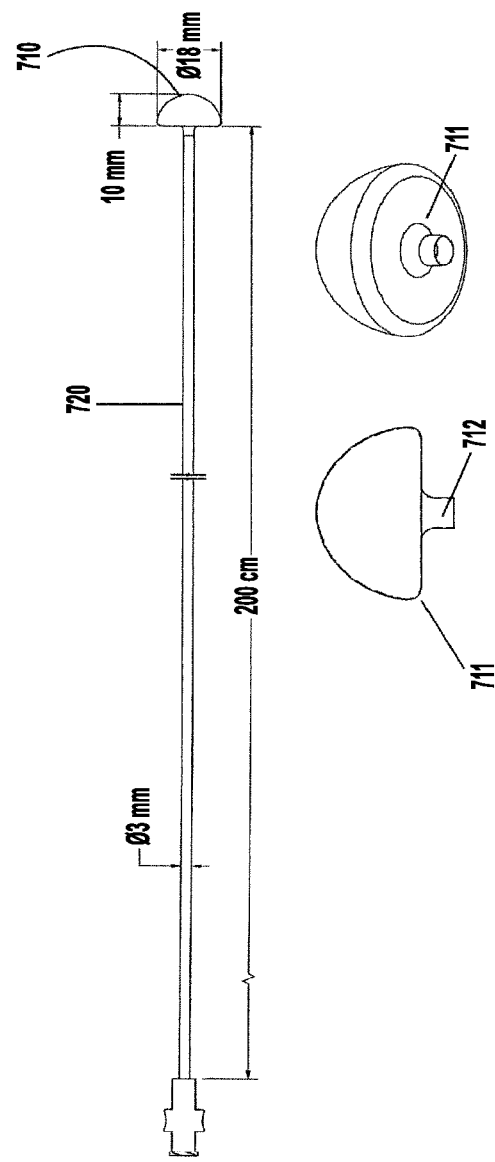
FIGS. 7a-c shows various views of yet another embodiment of a transparent dome with suggested dimensions, with FIG. 7a further showing a catheter.

FIG. 7a shows an additional embodiment of a transparent dome 710 and a catheter 720, with particular suggested dimensions. The catheter 720 should be long enough to extend through a scope, and accordingly is shown as 200 cm in length. The length may vary with the length of the scope. The transparent dome 710, from its flat region 711 to its distal tip may be 10 mm. The air intake portion 712 may be positioned at the center of the transparent dome 710, as shown in FIG. 7c, or as necessary to fit a particular catheter or scope opening. FIG. 7b shows a side view of the transparent dome 710. FIG. 7c shows an angled view of the transparent dome 710 from below.

Figure 8:
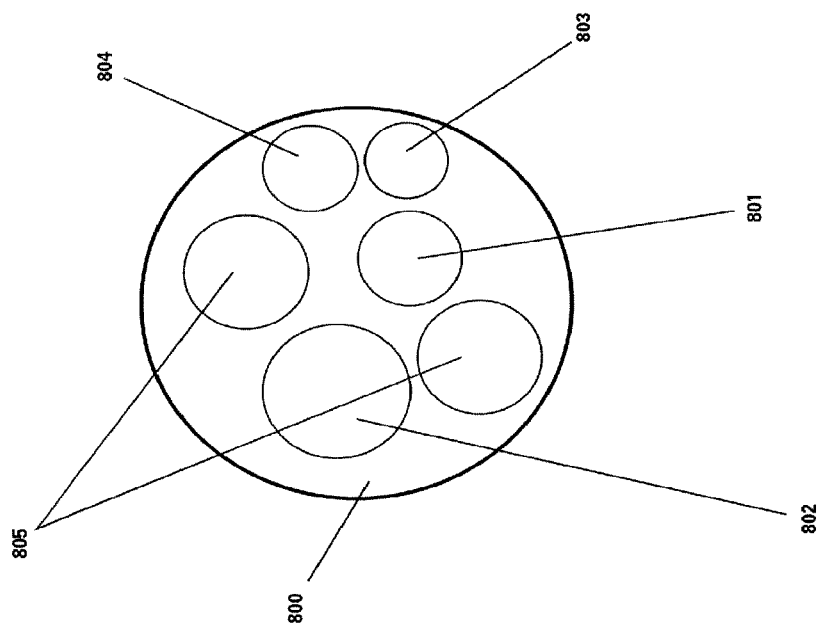
FIG. 8 shows a distal face of a scope such as is known in the art.

FIG. 8 shows a distal face 800 of a scope such as is known in the art. Features of the distal face 800 of the scope include a lens 801, an operative channel 802 offset from the center of the distal face 800, a water channel 803, an air channel 804, and light sources 805.

FIG. 9a shows a first view of the scope of FIG. 8 with an attached transparent dome 910 of the present invention. The transparent dome 910 comprises a single-layer membrane affixed to the distal end of the scope such that it covers the lens 801 as well an air channel 804 for inflating the transparent dome 910. The single-layer membrane may be, but is not limited to, a saran wrap-like plastic membrane, or any oilier suitable material. The affixation may be by a narrow rim of glue around at least a portion of the perimeter of the operative channel 802 and around the external surface of the scope just beneath a portion of the rim at tire circumference of the distal face 800. The single-layer membrane may be reusable and built into the scope. Unlike the balloon transparent domes (110; 210; 310; 410; 510; 610; 710; 1120; 1210; 1310) discussed elsewhere in this description, only a single layer of the transparent dome is distal to the lens 802. The single-layer membrane is affixed to the distal end of the scope such that it does nor cover the opening of the operative channel 802 through a portion of the distal face 800 of the scope. The single-layer membrane covers an approximately crescent-shaped region of the distal face 800 of the scope, the crescent-shaped region comprising approximately the entire face of the scope other than that portion of the face through which the operative channel 802 opens. The single-layer membrane may be attached to the scope by gluing or otherwise attaching it along the perimeter of the crescent-shaped region of the distal face 800, or by gluing or otherwise attaching it to the portion of the crescent-shaped region surrounding the operative channel 802 and along the outer circumference of the scope at a region slightly more, or as, proximal relative to the distal face 800.

Figure 9B:
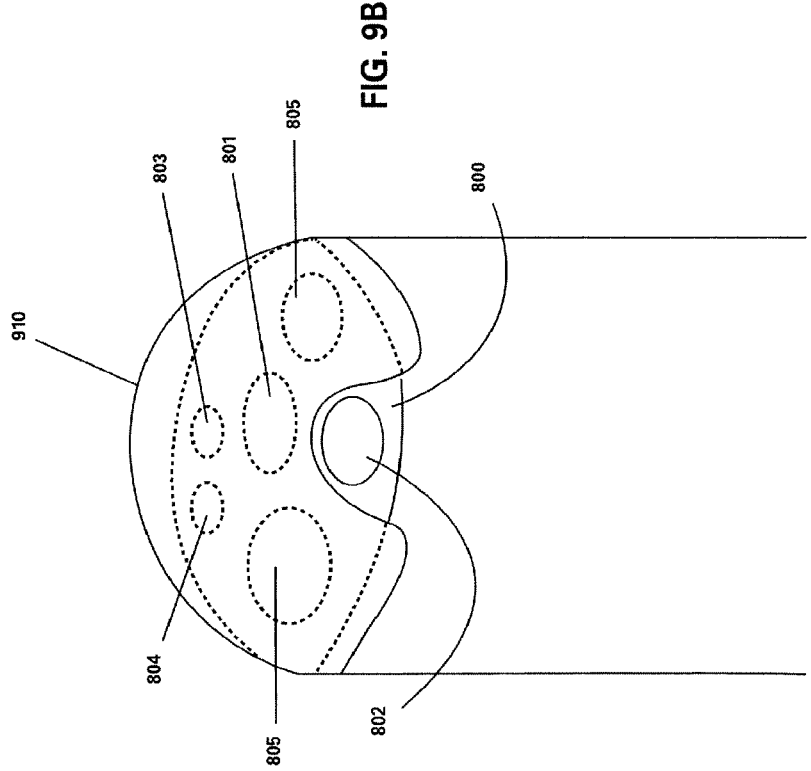

FIG. 9b shows a second view of the scope of FIG. 8 with an attached transparent dome 910 of the present invention. The transparent dome 910 is shown as inflated by the air channel 804.

FIG. 14 shows an embodiment similar to that of FIG. 9a, except the transparent dome 1410 comprises a single-layer membrane affixed to the distal end of the scope such that it covers only the lens 801 as well an air channel 804 for inflating the transparent dome 1410, as well as the intervening region between the lens 801 and the air channel 804. The transparent dome 1410 may lie flat on the lens 801 when deflated, which advantageously provides for easy washing of the transparent come 1410. The operative channel 802 is left open for any therapeutic maneuvers.

FIG. 15 shows an embodiment of an uninflated membrane covering the lens. It is a flat, see-through membrane flush against the lens. An operator can choose not to create a dome-shape structure by not inflating air. It is easy as easy to wash as a regular scope. It is reusable and washable with the scope.

FIG. 10a and FIG. 10b show a transparent dome 1010 according to the present invention in the form of a solid cap, and a scope to which the transparent dome 1010 may be attached to and detached from, at the distal end thereof. The particular shape and size of the solid cap should be configured to attach to a particular manufacturer's scope. FIG. 10a shows the transparent dome 1010 in the detached state, while FIG. 10b shows the transparent dome 1010 in the attached state. The transparent dome 1010 may be of any suitable solid material, such a solid plastic. When attached, the portion of the distal face 800 through which the operative channel 802 opens is not covered by the transparent dome 1010. The scope has at least one of an sir channel 804 and a water channel 803 opening out of portions of the distal face 800. At least one of these portions is not covered by the transparent dome 1010. Because the transparent dome 1010 is solid, it need not be inflated, and therefore no air channel need be covered by it. However, the lens 801 and light sources 805 are covered by the transparent dome 1010. When the transparent dome 1010 is attached to the scope, a seal 1011 is formed between the transparent dome 1010 and the scope that is water-tight. However, because file transparent dome 1010 does not need to be inflated, such as by an air channel, the seal 1011 is not air-tight. Alternately, the seal 1011 may be made air-light.

The transparent dome 1010, after being inserted along with the scope into a bodily cavity, may be allowed to have its exterior become dirtied by the bodily cavity. After this occurs, but while the scope and transparent dome 1010 are still inserted into the bodily cavity, the exterior of the transparent dome 1010 may be cleaned by water sprayed by the water channel 803 from the distal face 800 of the scope, allowing for easier viewing through the lens 801.

FIG. 11 shows an additional embodiment of a transparent dome 1110 in the form of a balloon along with a catheter 1130, therapeutic device 1140, and scope 1120. The transparent dome 1110 is held by a catheter 1130 at the catheter's side. The catheter comprises a textured portion 1132 and a bar 1133 for limiting distal movement of the transparent dome 1110 relative to the catheter 1130. The textured portion 1132 and bar 1133 may be made of arty suitable material, such as a plastic. The bar 1133 may clip-on, so as to be separately disposable and inexpensive to manufacture. In addition, either of the textured portion 1132 or the bar 1133 may be used in order to limit distal movement of the transparent dome 1110, rather than both. A therapeutic device 1140 is inserted through catheter 1130 to the distal side of the transparent dome 1110. An air channel 1131 is used to inflate and deflate the transparent dome 1110. The scope 1120 comprises an operative channel 1122 opening out of its distal face 1121, for passing the catheter 1130, transparent dome 1110 in its deflated state, and therapeutic device 1140. The scope 1120 also comprises, at its distal face 1121, a lens 1123, and lights 1124. Advantageously, because the transparent dome 1110 is held by the catheter 1130 and is not directly attached to the scope 1120, the transparent dome 1110 and/or catheter 1130 can be disposed of while reusing the scope 1120, saving money.

Figure 12A:
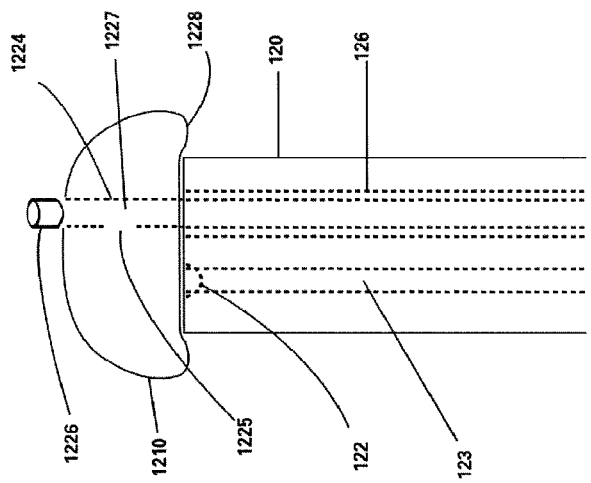
FIG. 12a shows a scope and an embodiment of a transparent dome in the form of a balloon having a therapeutic tip, the balloon being in a hyper-inflated state.
Figure 12B:
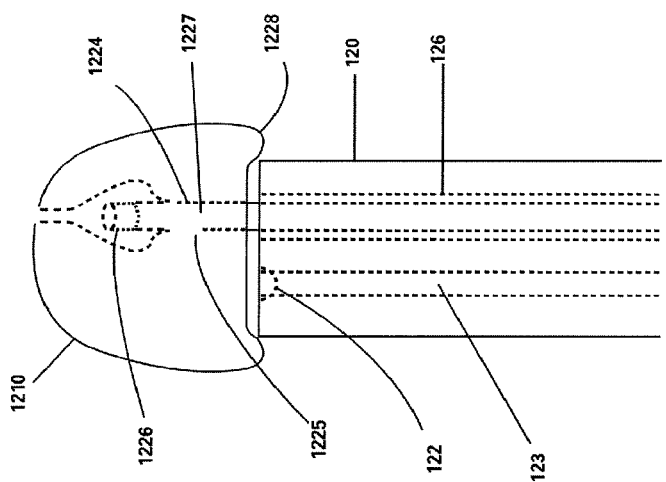
FIG. 12b shows the scope and transparent dome of FIG. 12a in an inflated but not hyper-inflated state.

FIGS. 12a and 12b show yet another embodiment of a transparent dome 1210 in the form of a balloon along with a catheter 1224, therapeutic device 1226, and scope 120. The catheter 1224 has an air channel 1227 and an air hole 1225 for inflating the transparent dome 1210. The catheter 1224 holds she transparent dome 1210 at its side. The scope has an operative channel 126 opening out of its distal face 121 for passing the catheter 1224, as well as a lens 122 at its distal face and a visual transmission channel 123 for passing the image or video received at the lens 122.

This embodiment, like the other embodiments, may be inserted into a bodily cavity. Before inflating the transparent dome 1210, the catheter 1224 holding the transparent dome 1210 may be inserted through the operative channel 126 of the scope 120. Initial inflation and/or hyperinflation of the transparent dome 1210 may occur after inserting the scope 120 and the transparent dome 1210 into the bodily cavity, or they may occur beforehand. After inflating the transparent dome 1210, at least the lens 122 on the distal face 121 of the scope 120 may be contacted with an exterior surface of the inflated transparent dome 1210. This exterior surface of the inflated transparent dome 1210 that will contact the lens 122 on the distal face 121 of the scope 120 may be generally flat. The contact may occur by pulling the catheter 1224 proximally relative to the scope 120, after the transparent, dome 1210 has been inflated.

The transparent dome 1210 is shown in FIG. 12a as being hyper-inflated to a first level of inflation such that the transparent dome 1210 extends to be more distal than, and generally surrounds, the distal tip of the catheter 1224, and the therapeutic device 1226. By surrounding die distal tip of the catheter 1224 and the therapeutic device 1226, the scope 120 and hyper-inflated transparent dome 1210 may be more easily and safely further inserted into a bodily cavity. Thus, after hyper-inflating the transparent dome as shown in FIG. 12a, the user may further insert the scope 120 and hyper-inflated transparent dome 1210 into the bodily cavity.

Then, as shown in FIG. 12b, the user may deflate the transparent dome 1210 a sufficient amount that the transparent dome 1210 no longer extends to be more distal than, and no longer generally surrounds, the distal tip of tire catheter 1224, or the therapeutic device 1226. Then, while viewing, through the visual transmission channel 123, the lens 122, and two walls of the transparent dome 1210, at least a portion of the bodily cavity, the user may use the therapeutic device 1226 at the distal end of the catheter 1224 on the portion of the bodily cavity being viewed. The therapeutic device 1226 being used on the portion of the bodily cavity being viewed extends, by way of the catheter 1224, from the distal face 121 of the scope 120 and exterior to the transparent dome 1210. A color filter, such as a green color filter, supplied by a transparent color, such as a green transparent color, of the transparent dome 1210 allows the user to identify, by way of the viewing, a feature of the bodily cavity made more prominent by the color filter or green color filter, such as a flat or other lesion.

The use of the therapeutic device 1225 may occur while at feast the distal tip of the transparent dome 1210 is to a pool of blood in the bodily cavity, or in direct contact with mucosa. As the transparent dome 1210 separates the lens 122 from the pool of blood or mucosa, vision of the bodily cavity is not greatly impaired by a red-out or like effect of blood or mucosa on the lens 122 itself.

FIGS. 13a-e show a method for using a transparent dome 1310 in the form of a balloon, scope, and catheter 1324 holding the balloon at the catheter's side. The scope has a lens 1301 for a user to view what is further distal than the scope's distal face 1300, and an operative channel 1302 for passing the catheter 1324. The catheter 1324 holds the transparent dome 1310 at its side. In this embodiment, the transparent dome is held at a hole along the catheter's side, through which air may flow to inflate the transparent dome 1310. However the transparent dome may be held in other manners, such as around the circumference of the catheter 1324. A retractable needle is shown as an example of a therapeutic device 1326 which may be inserted through the catheter. However, other therapeutic devices, either insertable through the catheter, or fixed at the distal tip of the catheter 1324, may be used.

In FIG. 13a, the catheter 1324 is shown withdrawn within the operative channel 1302, the transparent dome 1310 deflated and thereby fitting within the operative channel 1302 along with the catheter 1324.

Then, in FIG. 13b, the catheter 1324 is advanced distally relative to the scope such that the distal end of the catheter 1324 and the transparent dome 1310 are more distal than the distal face 1300 of the scope.

Then, in FIG. 13c, at such a time as when the distal tip of the catheter 1324 comes into view of the lens 1301, the transparent dome 1310 is inflated. Also, the therapeutic device 1326 is inserted through the catheter 1324 and the operative channel 1302 of the scope by moving it distally relative to the catheter 1324 and the operative channel 1302. This insertion may occur instead at other times before the therapeutic device 1326 is used on the bodily cavity.

Then, in FIG. 13d, by pulling the catheter 1324 proximally relative to the scope, at least the lens 1301 on the distal face 1300 of the scope is contacted with an exterior surface of the inflated transparent dome 1310. The therapeutic device 1326 is withdrawn into the scope during the pulling. The therapeutic device 1326 will therefore not get in the way during movement of the scope within the bodily cavity.

Then, in FIG. 13e, the transparent dome 1310 is slightly deflated and the catheter 1324 and the withdrawn therapeutic device 1326 are advanced distally relative to the scope such that the therapeutic device 1326 becomes exposed while the transparent dome 1310 continues to contact at least the lens 1301 on the distal face 1300 of the scope. The therapeutic device 1326 is now extending from the distal face 1300 of the scope and exterior to the transparent dome 1310, available for use, and may be used, on the bodily cavity under direct vision through the lens 1301 and the transparent dome 1310. After use, the therapeutic device 1326 and catheter 1324 may again be retracted into the scope.

As the catheter 1324 and therapeutic device 1326 may be chosen on the basis an identification of a particular lesion in a bodily cavity, a diagnostic and therapeutic procedure may be performed without the need to insert a new scope between the diagnostic portion of the procedure and the therapeutic portion of the procedure. In particular, a method of use for a transparent dome 1326 and a scope having a lens 1301 located at its distal face 1310 is presented, involving: inserting the scope into a bodily cavity, such as but not limited to a small intestine; using the lens 1301 of the scope, identifying a particular lesion of the bodily cavity; based on the identification of the particular lesion, advancing a catheter 1324 comprising a deflated transparent dome 1310 and a particular therapeutic device 1326 or tip chosen for its ability to treat the particular lesion, through an operative channel 1302 of the scope; inflating the transparent dome 1310; and under vision through the tens 1301 and the transparent dome 1310, treating the particular lesion with the particular therapeutic device 1326 of the catheter. Of course, a transparent dome that is part of a different catheter or the same catheter 1324 may be used, during the initial diagnostic portion, of the procedure.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A method for performing a gastrointestinal endoscopic imaging procedure within a non-insufflated bowel of a subject, comprising:
    a. inserting a gastrointestinal endoscope into the non-insufflated bowel of the subject, wherein the gastrointestinal endoscope comprises a distal face and a visual transmission channel for transmitting images or video information of the endoscope's operation through the transmission channel;
    b. providing an inflatable balloon;
    c. inflating the balloon;
    d. inserting the inflatable balloon into the non-insufflated bowel of the subject;
    e. positioning the inflated balloon in contact with the distal face of the gastrointestinal endoscope such that imaging using the visual transmission channel occurs through the inflated balloon;
    f. moving the gastrointestinal endoscope within the non-insufflated bowel while the inflated balloon is in contact with the distal face to image portions of the bowel wall along a length of the bowel and though the inflated balloon using the visual transmission channel.

2. The method of claim 1, wherein the gastrointestinal imaging procedure is a colonoscopy procedure.

3. The method of claim 1, wherein the gastrointestinal imaging procedure is a small bowel enteroscopy procedure.

4. The method of claim 1, wherein the patient is not medically sedated.

5. The method of claim 1, wherein the balloon is inflated using air.

6. The method of claim 1, wherein the balloon is inflated using fluid.

7. The method of claim 1, wherein the balloon is inflated prior to insertion into the non-insufflated bowel of the subject.

8. The method of claim 7, wherein the balloon is further inflated subsequent to insertion into the non-insufflated bowel of the subject.

9. The method of claim 1, wherein the inflated balloon is positioned in contact with the distal face of the gastrointestinal endoscope prior to insertion of the endoscope and balloon into the non-insufflated bowel of the subject.

10. The method of claim 9, wherein the gastrointestinal endoscope and balloon positioned in contact with the distal face of the gastrointestinal endoscope are inserted into the non-insufflated bowel of the subject.

11. The method of claim 1, wherein the balloon is transparent and comprises a proximal base and a distal dome rising from the base and having a tip.

12. The method of claim 11, wherein the height from the base to the tip is 1.0 centimeter (cm) or less.

13. The method of claim 11, wherein the base of the balloon covers at least the visual transmission channel of the endoscope such that imaging using the visual transmission channel of the endoscope includes the transmission of light through the base and the dome of the balloon.

14. The method of claim 13, wherein the balloon interior is devoid of internal structure that blocks light transmitted through the base and the dome for imaging using the visual transmission channel.

15. The method of claim 11, wherein the balloon further comprises an inflatable proximal projecting portion and wherein the method further comprises inflating the proximal projecting portion to engage the endoscope at a location proximal to the distal face of the endoscope to stabilize the balloon in its position in contact with the distal face of the gastrointestinal endoscope such that imaging using the visual transmission channel occurs through the inflated balloon while the proximal projecting portion is inflated and is engaging the endoscope.

* * * * *